United States Patent [19]

Fenton

[11] 4,078,567

[45] Mar. 14, 1978

[54] ILEOSTOMY POUCH AND MOUNTING ARRANGEMENT THEREFOR

[75] Inventor: Leonard Fenton, Beachwood, Ohio

[73] Assignee: Marlen Manufacturing and Development Co., Bedford, Ohio

[21] Appl. No.: 663,672

[22] Filed: Mar. 4, 1976

[51] Int. Cl.$^2$ .............................................. A61F 5/44
[52] U.S. Cl. .................................................. 128/283
[58] Field of Search ............. 128/283, 294, 295, 2 F; 119/95; 4/110, 121, 142

[56] References Cited

U.S. PATENT DOCUMENTS

| 2,595,934 | 5/1952 | Ginsburg | 128/283 |
| 2,684,676 | 7/1954 | Perry | 128/283 |
| 3,283,757 | 11/1966 | Nelsen | 128/283 |
| 3,528,420 | 9/1970 | Nielsen | 128/283 |
| 3,881,486 | 5/1975 | Fenton | 128/283 |
| 3,898,990 | 8/1975 | Nolan | 128/283 |

Primary Examiner—Robert W. Michell
Assistant Examiner—Henry S. Layton
Attorney, Agent, or Firm—McNenny, Pearne, Gordon, Gail, Dickinson & Schiller

[57] ABSTRACT

An ileostomy pouch and mounting device for the pouch are disclosed. The pouch comprises a bag having a drain opening at one end and a stoma-receiving opening adjacent its other end. An O-ring is sealed to the periphery of the stoma-receiving opening and has an integrally molded skirt flaring radially from the O-ring. A mounting ring is provided for the pouch and has an annular body-engaging face and an annular peripheral groove extending radially inwardly toward the axis of the ring. The O-ring is received in the groove entirely around the mounting ring to securely fasten the bag to the mounting ring.

4 Claims, 5 Drawing Figures

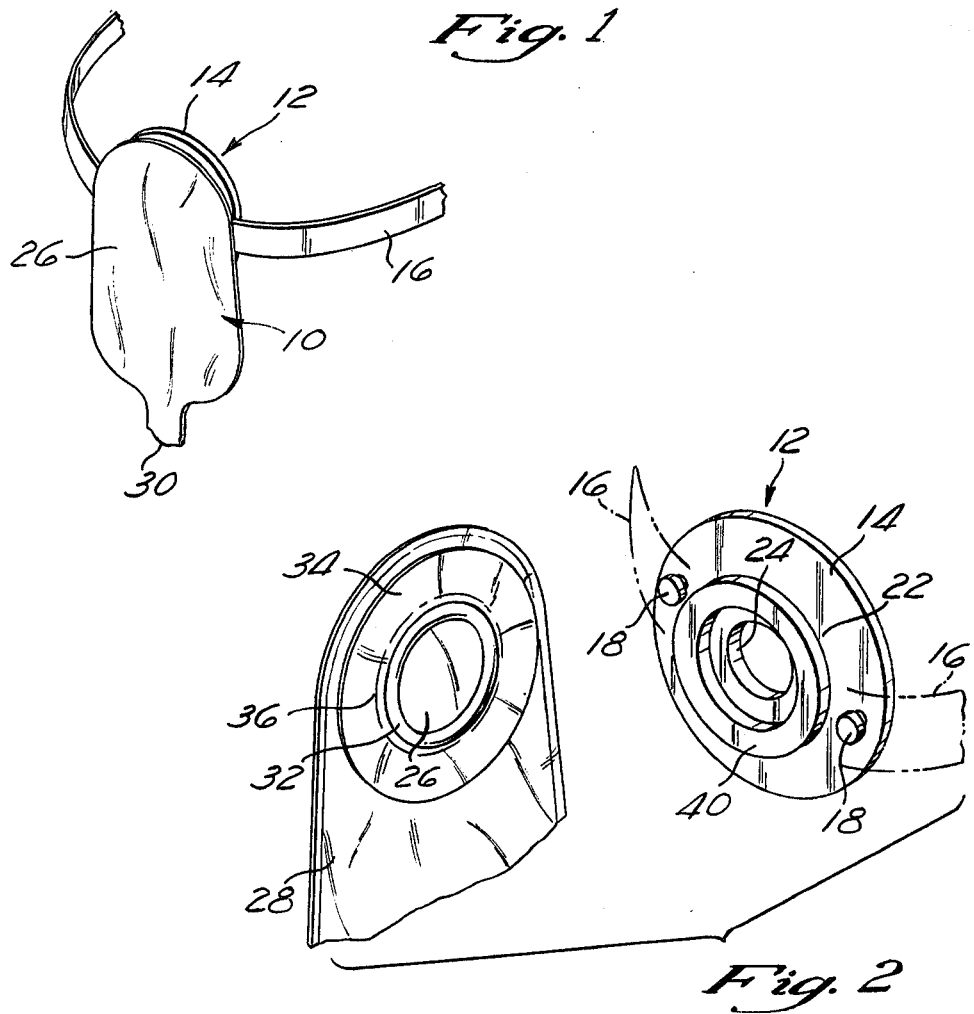
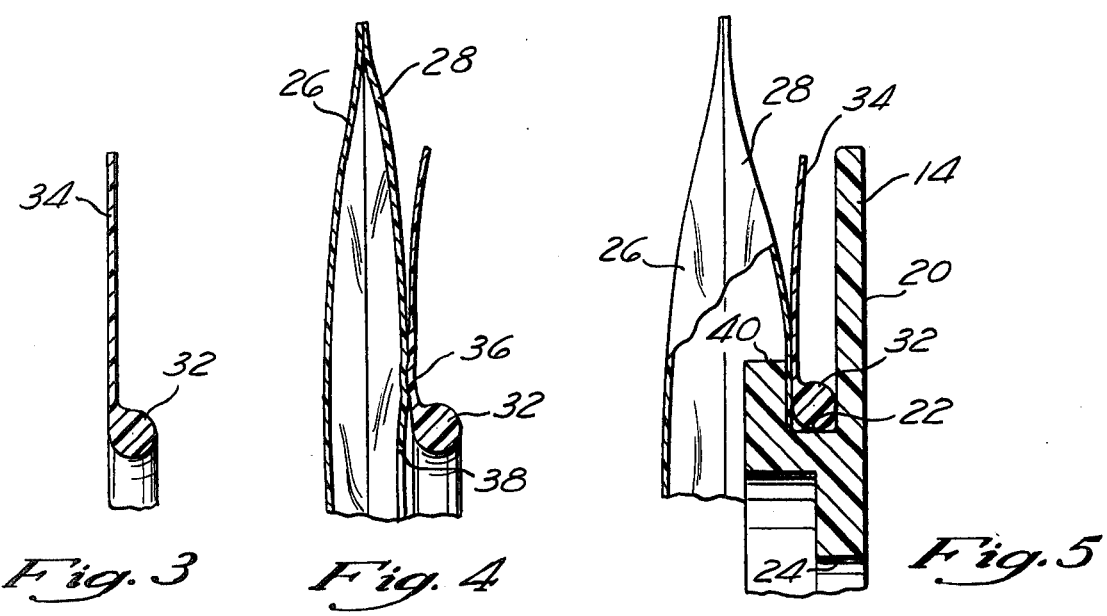

ILEOSTOMY POUCH AND MOUNTING ARRANGEMENT THEREFOR

BACKGROUND OF THE INVENTION

This invention relates to medical appliances, and more particularly to ileostomy receptacles which are adapted to be attached to the body of a patient and to receive material discharging from the patient's stoma.

An example of a prior art ileostomy receptacle is set forth in U.S. Pat. No. 2,784,718. In that patent, there is disclosed an ileostomy appliance which includes a pouch having a mounting device fixed thereto. The pouch includes two sheets of flexible material sealed together at their peripheries and having a drain opening and a stoma-receiving opening. A mounting ring is provided for the pouch which has an annular body-engaging face and an annular peripheral groove extending radially inwardly toward the axis of the ring. The bag is attached to the patient by slipping the ring into the stoma-receiving opening so that the periphery of the opening is seated within the peripheral groove. A separate O-ring is then wedged into the groove to clamp the bag opening in place.

Such arrangements, therefore, employ a separate O-ring and the manipulation of that O-ring to attach the bag to the mounting ring. Moreover, such loose O-rings tend to be misplaced or lost, thus necessitating the use of unreliable makeshift substitutes such as rubber bands and the like.

SUMMARY OF THE INVENTION

This invention overcomes the prior art problems by providing a mounting bag having its own O-ring heat sealed thereto. A mounting ring for the pouch has an annular body-engaging face and an annular peripheral groove extending radially inwardly toward the axis of the ring. The O-ring portion of the bag is received in the groove entirely around the mounting ring to securely fasten the bag to the mounting ring. As an aid in mounting and dismounting the bag to and from the ring, an integrally molded skirt flares radially from the O-ring so that it may be grasped during the mounting and dismounting operations. The provision of an O-ring heat sealed to the pouch provides an arrangement wherein it is easier to assemble the pouch on the mounting ring while the ring is attached to the body.

BRIEF DESCRIPTION OF THE DRAWING

FIG. 1 is a fragmentary, perspective view of a bag attached to its mounting ring;

FIG. 2 is an exploded, fragmentary, perspective view showing the bag removed from the mounting ring;

FIG. 3 is a fragmentary, cross sectional view of the O-ring and its flaring skirt;

FIG. 4 is a fragmentary, cross section of the O-ring and skirt heat sealed to the bag; and FIG. 5 is a fragmentary, cross sectional view of the bag mounted on the mounting ring.

DETAILED DESCRIPTION OF THE DRAWINGS

There is disclosed an ileostomy pouch 10 mounted on a mounting device 12. The mounting device 12 includes a mounting ring 14 which is held firmly against the abdomen by means of a belt 16. As may be seen most clearly in FIG. 2, the belt is attached to the ring by projecting lugs 18 to which the ends of the belt are attached. The mounting ring 14 has an annular body-engaging face 20 and an annular peripheral groove 22 which extends radially inwardly toward the axis of the ring. The ring 14 has a stoma-receiving opening 24.

Mounted on the ring 12 is the ileostomy pouch 10 which includes two flat walls 26 and 28 heat sealed together at their peripheries. The walls 26 and 28 may be of the illustrated single-ply type, or they may be double walls, as is set forth in U.S. Pat. No. 3,385,298. The walls may be of vinyl plastic or a rubber or rubber-like material. A discharge opening 30 is provided from which the contents of the pouch may be discharged. The opening 30 may be closed by folding the neck back upon itself and applying any suitable form of clip (not shown).

An O-ring 32 having an integral flaring skirt 34 is heat sealed to the face 28 at an annular zone 36 so that it becomes integrally connected to the pouch 10 with the O-ring in substantial coaxial alignment with an opening 38 in the face 28. The O-ring is mounted in the groove 22 by stretching the ring over an annular flange 40 on the ring 12, as is illustrated in FIG. 5. As an aid in performing this operation, the skirt 34 may be grasped by the user. It should be appreciated, however, that the skirt may be eliminated if desired. The mounting operation may be performed more easily than the mounting operation where a separate O-ring is provided and there is no likelihood of losing the integral O-ring 32. Furthermore, the use of an integral O-ring facilitates the mounting of the pouch to the ring while the ring is attached to the patient.

Although a preferred embodiment of this invention is illustrated, it is to be understood that various modifications and rearrangements of parts may be resorted to without departing from the scope of the invention.

What is claimed is:

1. An ileostomy pouch comprising a bag of elastic sheet material having a drain opening in one end and a stoma-receiving opening adjacent its other end, and an O-ring of stretchable elastic material having an integrally molded skirt flaring radially outwardly therefrom, a portion of said skirt being sealed on the bag to the periphery of said stoma-receiving opening, said O-ring having a circular cross section, the molded skirt having a generally flat configuration lying in a generally radial plane and having a thickness substantially less than the diametral thickness of the O-ring cross section, the radial extent of the skirt beyond the portion thereof sealed to the bag being free of the bag and of sufficient size to be grasped by the user to aid in installing the bag by stretching the O-ring over an annular flange of a mounting ring to position the O-ring radially in a groove of the mounting ring associated with the annular flange to thereby lock the bag on the mounting ring.

2. An ileostomy pouch comprising a bag of elastic sheet material having a drain opening in one end and a stoma-receiving opening adjacent its other end, a mounting ring for said pouch having an annular body-engaging face, an annular peripheral groove in said ring extending radially inwardly toward the axis of the ring, and an O-ring of stretchable elastic material having an integrally molded skirt flaring radially outwardly therefrom, a portion of said skirt being sealed on the bag to the periphery of said stoma-receiving opening, said O-ring having a circular cross section, the molded skirt having a thickness substantially less than the thickness of the O-ring cross section, the radial extent of the skirt beyond the portion thereof sealed to the bag being free of the bag and sufficient in size to be grasped by the user to aid in installing the bag by stretching the O-ring over the mounting ring for positioning radially into said peripheral groove, said O-ring being received in said groove entirely around said mounting ring and thereby locking the bag to the mounting ring.

3. An ileostomy pouch according to claim 2, wherein the skirt portion of said O-ring is heat sealed to the periphery of said stoma-receiving opening.

4. An ileostomy pouch according to claim 3, wherein said bag is composed of a vinyl material.

* * * * *